United States Patent

Schaad et al.

(10) Patent No.: US 6,410,223 B1
(45) Date of Patent: Jun. 25, 2002

(54) DIRECT POLYMERASE CHAIN REACTION ASSAY, OR BIO-PCR

(75) Inventors: Norman W. Schaad, Myersville, MD (US); Nikolas J. Panopoulos, Iraklio-Crete (GR); Efstathios Hatziloukas, Frederick, MD (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 08/334,085

(22) Filed: Nov. 4, 1994

(51) Int. Cl.$^7$ ................................................ C12Q 1/68
(52) U.S. Cl. ............................................ 435/6; 435/34
(58) Field of Search ................................ 435/6, 31, 34, 435/91.1, 820; 436/504; 536/23.1; 935/19, 78

(56) References Cited

U.S. PATENT DOCUMENTS

| | | | |
|---|---|---|---|
| 4,358,535 A | * 11/1982 | Falkow | 435/5 |
| 4,683,202 A | 7/1987 | Mullis et al. | |
| 5,234,824 A | * 8/1993 | Mullis | 435/91 |
| 5,436,144 A | * 7/1995 | Stewart et al. | 435/91.2 |

OTHER PUBLICATIONS

Schaad et al., Plant Pathology, Beyond 2000, Abstracts of Presentations, Nov. 8, 1993.*

Maniatis T., Molecular Cloning, A Lab Manual Cold Spring Harbor Lab 1982.*

Petitjean J., Specific Detection of Enteroviruses . . . J of Clin Microbiol 28 (2) 1990 pp. 307–311.*

Oshiro R., Modification of Reagents in the Enviroamp . . . Can J Microbiol 40 (6) 1994 pp. 495–499.*

Nitschke et al., *BioTechniques*, vol. 14(6), pp. 914–916 (1993).

Udy et al., *Technique—A J. of Methods in Cell and Mol. Biol.*, vol. 2(2), pp. 88–92 (1990).

Scaad et al., *Plant Pathology, Beyond 2000*, Abstracts of Presentations (Nov. 1993).

Fitter et al., *J. of Applied Bacteriology*, vol. 73, pp. 53–59 (1992).

Rossen et al., *Int. J. of Food Microb.*, vol. 17, pp. 37–45 (1992).

* cited by examiner

*Primary Examiner*—Ralph Gitomer
(74) *Attorney, Agent, or Firm*—M. Howard Silverstein; John D. Fado; Janelle S. Graeter

(57) ABSTRACT

A novel polymerase chain reaction (PCR) technique which can specifically detect viable cells of a target cell or microorganism has been developed. The method combines a biological preamplification on growth medium with direct PCR and eliminates DNA extraction steps required for conventional PCR methods.

4 Claims, 2 Drawing Sheets

DIRECT POLYMERASE CHAIN REACTION ASSAY, OR BIO-PCR

BACKGROUND OF THE INVENTION

1. Field of the Invention

Existing polymerase chain reaction (PCR) techniques have provided sensitive and specific means for detecting DNA-containing analytes. The need for time-consuming and expensive Southern blots for detecting very small amounts and a requirement for cell lysis and DNA extraction, however, have provided an incentive for simplification of the procedure. This invention relates to a two-step direct PCR method which combines biological and enzymatic amplification of PCR targets and simplifies the procedures for sample processing.

2. Description of the Prior Art

Conventional hybridization assay methods utilizing DNA as the means for determining the presence of a given analyte in a sample have been practiced for many years, but there have been problems and drawbacks associated with this method, such as a lack of sensitivity and specificity as well as the time required to carry out the assay. The advent of the polymerase chain reaction eliminated many of these concerns, e.g. sensitivity has been increased to the extent that the detection of a single cell in a sample is theoretically possible, but, while specificity and sensitivity have been increased, the method often requires time-consuming and expensive Southern blots in order to detect small numbers of cells.

In addition, some samples, such as soil (Bej et al. 1991. *Appl. Environ. Microbiol.* vol. 57, pp. 1013–1017), food products (Rossen et al. 1992. *Int. J. Food Microbiol.* vol. 17, pp. 37–45) and plant leaves (Demeke and Adams. 1992. *Biotechniques,* vol. 12, pp. 332–334; Rowhani et al. 1993. *Phytopathology.* vol. 83, pp. 749–7535), may also contain inhibitors of PCR (Prosen et al. 1993. *Phytopathology.* vol. 83, pp. 965–970; Rasmussen and Wulf. 1991. Detection of *Pseudomonas syringae* pv. *pisi* using PCR. pp. 369–376, and Tourte and Manceau. 1991. Direct detection of *Pseudomonas syringae* pathovar *phaseolicola* using the polymerase chain reaction (PCR). pp. 402–403 both in: *Proceedings 4th International Working Group on Pseudomonas syringae Pathovars.* Internat. Soc. Plant Pathology Committee on Phytopath. Bact. and Univ. di Firenze, Inst. di Pathologia, Florence, Italy) which are not easily removed by standard extraction procedures. For example, in studies (Prosen et al., supra) utilizing DNA from seed extracts containing relatively small numbers of pathogen, it was determined that cfu's (on average 12 cfu/reaction) gave variable results in replicate amplifications. In contrast, tests with direct nested PCR carried out with culture aliquots without prior DNA extraction consistently gave strong PCR bands.

Another general problem with PCR techniques is the inability to differentiate between dead cells and live cells, which is important in many phytosanitary applications.

SUMMARY OF THE INVENTION

To overcome these problems we have developed a novel technique which can specifically detect viable cells in any environmental sample. To accomplish this goal, we have combined biological preamplification on a growth medium with direct PCR by introducing a plating step prior to PCR analysis. This modification, which we have named BIO-PCR, provides the benefit of biological amplification of PCR targets prior to enzymatic amplification. The technique significantly improves detection in samples with low levels of contamination and greatly reduces the detection of dead cells and/or free DNA.

In accordance with this development, it is the object of the invention to provide a novel assay method which combines a culture step and a direct polymerase chain reaction step resulting in a method having increased specificity and sensitivity and decreased interference from contaminants such as inhibitors and dead cells.

DETAILED DESCRIPTION OF THE INVENTION

Figure 1:
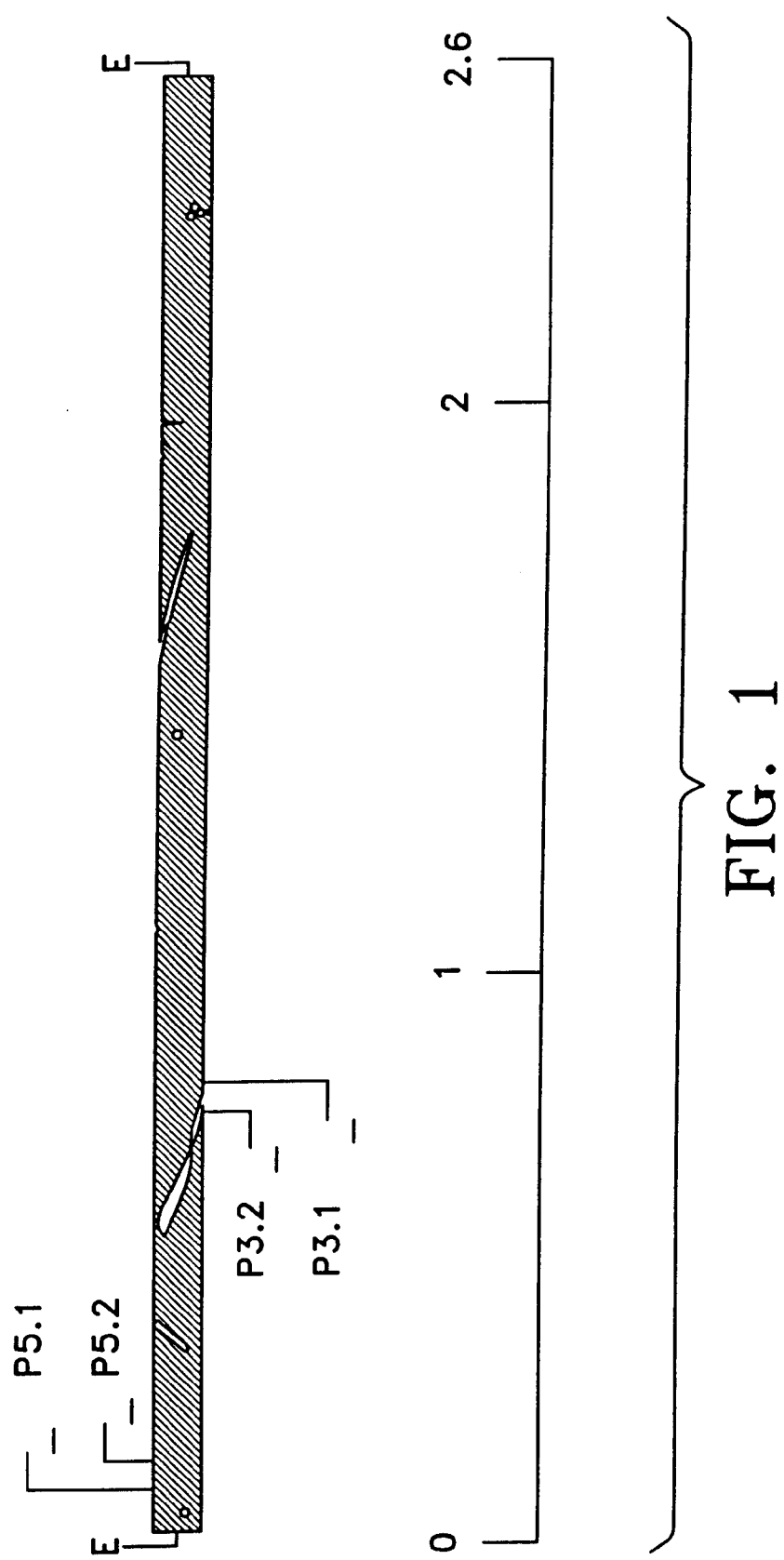
FIG. 1 shows the position of the PCR primers in the 2.6 kb EcoRI tox cluster segment of *Pseudomonas syringae* pv. *phaseolicola*.
Figure 2:
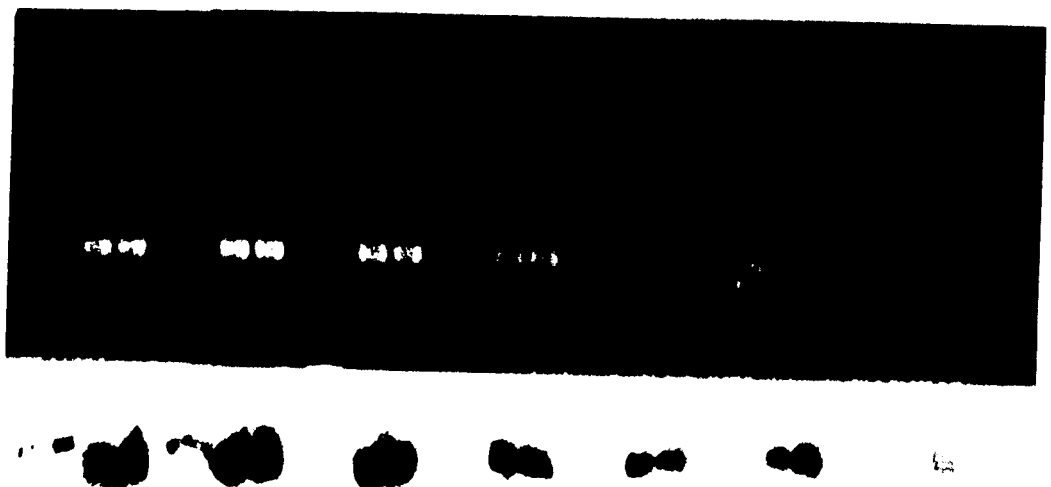
FIG. 2 shows the detection threshold of *Pseudomonas syringae* pv. *phaseolicola* DNA by standard and nested PCR. A group of four lanes is shown for each DNA concentration. The left two lanes in each group correspond to duplicate PCR reactions with the external primers and the two right lanes to duplicate reactions with nested primers. The right most lane shows the sterile distilled water control. The upper panel shows the ethidium bromide stained bands (white on black background) and the lower panel the bands detected by Southern hybridization (black bands on white background). The size of the standard and nested PCR products is 0.5 and 0.45 kb, respectively. Numbers on the top indicate picograms of DNA used per amplification reaction.

The invention is useful in any biological application where the samples of interest can be cultured and where conventional PCR methods can be effectively carried out. Advantages over conventional PCR include the detection of live cells only, a 100- to 1000-fold increase in sensitivity, the elimination of PCR inhibitors often associated with environmental samples, thus eliminating false negatives and the elimination of the need for DNA extraction prior to amplification. Normally, PCR will detect dead cells because DNA is very stable; however, BIO-PCR detects only those cells which are alive, thus eliminating false positive dead cells. The sensitivity is increased by preamplifying the target organisms biologically using 100- to 500-$\mu$l samples (current PCR methods use only 10- to 20-$\mu$l samples), resulting in the detection of as few as 2–3 cells per ml of sample.

Analytes which are effectively detected by the invention include any DNA- or RNA-containing living organisms, such as microorganisms or cells, which can be grown in culture. These organisms include but are not limited to plant and animal cells, bacteria, viruses, plasmids, fungi and mycobacteria.

The method is a two-step process carried out by 1) culturing a sample suspected of containing analyte in order to preamplify, or biologically increase, the number of cells or microorganisms in the sample and 2) performing direct PCR on the cultured sample.

The culturing step is carried out under conditions which are appropriate for the particular organism of interest. Selective or non-selective media may be used. This step accomplishes several different objectives: it reduces or eliminates the detection of dead propagules and cell-free DNA, effectively removes PCR inhibitors that may be present in the original sample, and permits the biological amplification of PCR targets prior to their enzymatic amplification. Agar plating is similar in principle to liquid enrichment techniques (e.g., Fitter et al. 1992. *J. Appl. Bact.* vol. 73, pp. 53–59), but is advantageous in that it apparently removes PCR inhibitors more effectively due to diffusion into the agar matrix. Other formulations of media may increase the recovery of target cells from samples, thereby increasing the sensitivity of the method even more. The use of cells washed from agar media for amplification increases the sensitivity of detection in samples having low levels of cells by allowing use of a greater sample volume (100–500 µl for agar plating versus 10 µl for conventional PCR).

The amount of time which the samples are allowed to incubate during culture is determined by growth rate and the number of organisms or cells which are desireable for PCR. These parameters are easily determined by one of skill in the art based on the individual characteristics of the organism. For example, microorganisms such as *Escherichia coli* (*E. coli*) could be cultured for as little as 6–8 hours due to their rapid growth rate. The PCR procedure is sufficiently sensitive that a large number of organisms is not required for effective detection.

Sample organisms are removed from culture by either washing the plates (for plated samples) or removing aliquots from liquid cultures and washing by filtration, centrifugation or other conventional means.

The enzymatic amplification step is carried out by direct PCR. The conventional PCR procedure is well-known in the art (described by Mullis, U.S. Pat. No. 4,683,202, herein incorporated by reference), with direct PCR omitting cell lysis and DNA extraction steps. Essentially, nucleic acid sequences contained within the target organism are amplified using appropriate primers, or oligonucleotides, followed by detection of the amplified product by any effective detection means. Dot blot hybridization and ethidium bromide (EtBr) staining of final PCR products give consistently good results. If the gene which is the amplification target is present in the organism as a single copy, the use of nested primers is advantageous. The examples presented hereinbelow describe such a procedure. However, when multiple-copy genes or highly repetitive target sequences are present, single pairs of primers may be sufficient.

An additional advantage of BIO-PCR is that quantitative data on viable pathogen populations can be obtained by dilution-end-point analysis if samples are not heavily contaminated with saprophytes. Although quantitation of pathogen contamination is currently not necessary in some instances because a "zero tolerance" policy is followed (Webster et al. 1983. *Plant Dis.* vol. 67, pp. 935–939), quantification of pathogen propagules would be desirable in other cases.

The elimination of DNA extraction is also advantageous for several reasons. The use of hazardous chemicals such as phenol is avoided; cells are not lost during DNA extraction procedures; and the method is considerably less technical due to the elimination of the DNA extraction and Southern hybridization steps. In addition, samples can be prepared, plated at the site of origin, and the plates can either be mailed immediately to a PCR testing laboratory or incubated, plate washings collected, pooled if desired and mailed frozen. Immediate mailing of the agar plates would compensate for the incubation time required.

While the invention is effective for the detection of any cultivatable cell or microorganism, it is exemplified herein for purposes of description by the plant pathogen *Pseudomonas syringae* pv. *phaseolicola* (*P.s. phaseolicola*), a serious seedborne bacterial pathoghen of beans which causes halo blight disease worldwide (Taylor et al. 1979. *Ann. Appl. Biol.* vol. 93, pp. 167–172; Webster et al., supra). A PCR (27) technique which amplifies a segment of the genomic phaseolotoxin gene cluster (Peet et al. 1986. *J. Bacteriol.* vol. 166, pp. 1096–1105) by using a single pair of primers was recently reported (Prosen et al., supra). The method is specific for *P.s. phaseolicola,* but usually requires Southern blots in order to detect the small numbers of pathogen colony forming units (cfu) found in some seed extracts. Using BIO-PCR, however, this requirement can be eliminated. In addition, seed lots having low levels of saprophytic bacterial contamination can be assayed by agar plating seed extracts (Mohan and Schaad. 1987. *Phytopathology.* vol. 77, pp. 1390–1395), removing suspected colonies of *P.s. phaseolicola* and testing by direct PCR. In seed lots where the numbers of saprophytes are larger, the extracts should be diluted to approximately $10^{-2}$ in order to reduce the numbers of saprophytes so that colonies of *P.s. phaseolicola* can be easily identified. The agar plating step introduced prior to PCR analysis provides the benefit of biological amplification of the PCR targets in the seed extract. The technique thus greatly improves detection of the pathogen in seed washings with low levels of contamination and greatly reduces the chances of detecting dead cells or free DNA.

The detection threshold achieved by BIO-PCR was $3\times10^3$ cfu/sample of 3,000 seeds when the seeds were washed in 1,500 ml buffer, and 5 samples of 100 μl were plated. This means that contaminated seeds must contain greater than $3\times10^3$ cfu because the extraction efficiency is not 100%.

This is the first report of the successful detection of a pathogen in the range of 2–3 cells/ml of original sample by direct PCR (i.e. without extraction of DNA). Such high sensitivity would not be possible without BIO-PCR due to dilution factors alone.

The procedure thus provides improvements to the previous PCR method for the detection of *P.s. phaseolicola* in bean seed (Prosen et al., supra), specifically, a plating step on ordinary (non-selective) agar medium and direct amplification of plate washes without prior DNA extraction. The technique has many advantages over standard PCR methods for routine detection of seedborne pathogens, among them being increased sensitivity, simplicity, and detection of live cells only. Accordingly, it facilitates the implementation of PCR-based screening of commercial bean seed lots for *P.s. phaseolicola* contamination, especially in laboratories that are not fully equipped or lack personnel trained in various techniques connected with PCR applications. Additionally, it is also be very useful for studying epidemiology, host-pathogen relations, biopesticide risk assessment, and environmental sampling including soil and water.

The following examples are intended only to further illustrate the invention and are not intended to limit the scope of the invention as defined by the claims.

EXAMPLES

Example I

Bacterial Strains and Growth Conditions

*P.s. phaseolicola* strain C-199 originated from bean plants in Idaho and was used in previous studies on DNA probes (Schaad et al. 1989. *Phytopathology.* vol. 79, pp. 1989) and PCR (Prosen et al., supra). *P.s. phaseolicola* strains NPS3121 and 4419 have been described previously (Peet et al., supra). Phenotypically $tox^-$ *P.s. phaseolicola* strains were obtained from K. Rudolph (Institut für Pflanzenpathologie und Pflanzenschutz, George August Universität, Bottingen, Germany): i) GSPB592 and GSPB593, single colony isolates from strain 0458 (M. L. Moffett, Department of Primary Industries, Brisbane, Australia), which was originally isolated from *Glycine weightii;* ii) GSPB792, re-isolated from bean after inoculation with strain W51–32, a tox⁻ strain originally isolated in the Netherlands by J. C. Walker, Department of Plant Pathology, University of Wisconsin, Madison; and iii) strains GSPB606, GSPB607 and GSPB612, isolated by K. Rudolph from plants in field plots that had been inoculated with strain GSPB792. All cultures were maintained on King et al.'s medium B (KB) agar slants and grown in Luria-Bertani (LB) liquid medium. Permanent stocks were stored at −80° C. Unless otherwise stated, Pseudomonas strains were grown at 28° C.

Example II

Oligonucleotide Primers

The following primers were selected from a 2.6 kb segment of the tox region (Prosen et al. 1990. *Phytopathology.* vol. 81, p. 1159; Prosen et al., 1993, supra) that has been sequenced (Hatziloukas and Panopoulos, unpublished), by using the primer analysis program OLIGO (National Biosciences, Hamel, Minn.):

| | |
|---|---|
| 5'AGCTTCTCCTCAAAACACCTGC3' | SEQ ID NO: 1 |
| 5'TGTTCGCCAGAGGCAGTCATG3' | SEQ ID NO: 2 |
| 5'TCGAACATCAATCTGCCAGCCA3' | SEQ ID NO: 3 |
| 5'GGCTTTTATTATTGCCGTGGGC3' | SEQ ID NO: 4. |

The binding sites for primers 1 and 2 are located outside those of primers 3 and 4 in the above segment (FIG. 1); therefore, the first two primers are referred to as the external primer pair (EPP) and the latter two as internal primer pair (IPP).

Example III

Comparison of DNA Extraction Methods to Direct PCR

To determine the efficacy of a simplified method for sample processing, the following methods were tested: i) the hexadecyltrimethylammonium bromide (CTAB) method (Bej et al., supra) modified by omitting the second phenol/chloroform/isoamyl alcohol deproteinization step and adding 5 µg of yeast tRNA (Sigma Chemical Co., St. Louis, Mo.) per sample to facilitate nucleic acid precipitation (Prosen et al., 1993, supra); ii) aliquots of cell suspensions were boiled for 10 min and placed immediately on ice before amplification; iii) cell suspensions were boiled for 10 min, tRNA and isopropanol were added, and further treated as in the CTAB method above; iv) direct amplification of small aliquots of bacterial cultures was performed without prior DNA extraction or other sample processing (direct PCR). Identical aliquots from the same liquid culture of *P.s. phaseolicola* C-199 (adjusted to contain between 4–10 cfu) were used in the above four procedures. Samples were amplified by nested PCR utilizing the primers described in Example II, and the products were analyzed by electrophoresis, as described below. Six replicates, each a separate DNA or bacterial preparation, were tested in the first experiment and four in the second experiment.

Direct PCR gave the most consistent and reproducible results. In one experiment, out of six samples tested, 6, 2, 0 and 3 were scored positive by direct PCR, modified CTAB, boiling only, and boiling plus precipitation, respectively. In another experiment, out of four samples tested, 3, 4, 0 and 0 were scored positive by direct PCR, modified CTAB, boiling, and boiling followed by precipitation, respectively.

Example IV

DNA Probes and Hybridization

Two different probes were used for Southern hybridization analysis. i) For the determination of sensitivity of the method and for the detection of the pathogen in water extracts of bean seed, the probe was a 0.45 kb DNA fragment that was synthesized and labeled by PCR as follows: 40 ng of *P.s. phaseolicola* C-199 genomic DNA, were amplified by using the EPP, as described below. A 2-µl aliquot of a 1:10 dilution of the product of the first amplification round was re-amplified under identical reaction and cycling conditions but using the IPP and a deoxynucleotide triphosphate mixture containing digoxigenin-11-dUTP, as the labeling nucleotide (Boehringer-Mannheim). The resulting DNA was used as hybridization probe following the protocol recommended by the supplier of the labeling nucleotide. ii) For the hybridization analysis of the genomic DNA's from the *P.s. phaseolicola* tox⁻ strains, as well as their nested PCR products (see Example VIII below), we used as probe the 2.6 kb-EcoRI fragment (FIG. 1), derived from the tox cluster of *P.s. phaseolicola* NPS3121, described earlier (20–22,28). This fragment was labeled by using a non-radioactive DNA labeling kit (Boeringer-Mannheim), according to the supplier's instructions.

Capillary transfer and cross-linking of DNA to Nytran membranes (Boeringer-Mannheim) was carried out following standard procedures (Ausubel et al. 1987. *Current Protocols in Molecular Biology.* John Wiley & Sons, Inc. New York; Maniatis et al. 1989. *Molecular Cloning, a Laboratory Manual.* Cold Spring Harbor Laboratory, Cold Spring Harbor, N.Y.). Prehybridizations and hybridizations were carried out according to the instructions of the membrane supplier (Boeringer-Mannheim) and labeled nucleic acids were detected by using the "Genius™" Immunoblot kit (Boeringer-Mannheim).

Example V

PCR Protocols

Standard PCR reactions were carried out by using the EPP. Reactions were routinely done in quadruplicate with the following profile: an initial 2 min incubation at 94° C., a manual "hot start" step (Chou et al. 1992. *Nucl. Acid Res.* vol. 20, pp. 1717– 1723) at 80° C., 25–30 cycles (1 min at 94° C., 1 min at 58° C. and 2 min at 72° C., and a final extension step of 8 min at 72° C. Double-nested (hereafter referred to simply as nested) PCR reactions consisted of standard PCR with the EPP, followed by reamplification of 2 µl of 10-fold diluted products with the IPP for 25 cycles. All amplifications were carried out in 0.5 ml thin-wall tubes, in a final volume of 50 µl, and under a layer of mineral oil (Perkin Elmer-Cetus, Norwalk, Conn.) in a Perkin Elmer-Cetus Model 480 DNA Thermocycler. Reaction mixtures contained the following ingredients at the given final concentrations: 10 mM Tris-HCl, pH 8.3; 50 mM KCl, 1.5 mM MgCl$_2$; 0.001% gelatin; 80 µM each of DATP, DCTP, dGTP, and dTTP; 0.2 units of Taq DNA polymerase (Perkin Elmer-Cetus); and 0.5 µM of each primer. Stock solutions were stored in aliquots at −20° C. and never used more than five times. Sterile double distilled water (SDDW) was used for all solutions and dilutions above. To help avoid carry-over contamination, duplicate samples and SDDW controls were routinely included in each experiment and PCR conducted in a separate laboratory. All experiments were repeated at least once. Amplification products were analyzed by electrophoresis on agarose gels that were either stained with EtBr, as described (Mohan and Schaad, supra), and/or blotted onto Nytran membranes for hybridization. To detect possible artifacts due to carryover contamination of PCR products, duplicate samples and SDDW controls were routinely included in each experiment. In addition, all experiments were repeated at least once and PCR reaction mixtures were prepared in a separate laboratory.

Example VI

Sensitivity of Detection

The sensitivity threshold for the external and internal primer pairs in the standard and nested PCR format was determined as follows: i) triplicate 0.1-ml samples of $10^{-6}$, $10^{-7}$, $0.5 \times 10^{-7}$ and $10^{-8}$ serial dilutions of a liquid culture of *P.s. phaseolicola* NPS3121 (initial $OD_{600}=0.1$) were plated onto KB plates to determine colony forming units (cfu)/ml. Duplicate 1.0-ml aliquots from each dilution were stored at −20° C. Genomic DNA was extracted from these stored aliquots by the CTAB method modified as described in Example III above and adding 5 µg of yeast tRNA per sample to facilitate nucleic acid precipitation. The final nucleic acid pellet was rinsed with 70% ethanol (−20° C.), dried, and re-suspended in 30 μl of TE buffer. PCR analysis was carried out in 10-μl aliquots of these extracts. ii) DNA was extracted from a liquid culture ($OD_{600}$=0.1) by the modified CTAB method (without tRNA addition) and its concentration determined spectrophotometrically (Jansing and Rudolph. 1990. *J. Plant Dis. & Protec.* vol. 97, pp. 42–55). Serial dilutions of this extract were made in TE buffer and 10-μl aliquots used for PCR analysis. PCR products were analyzed as described above.

Both the standard and nested PCR formats yielded single discrete product bands (0.5 kb with the external primers and 0.45 kb with the internal primers), as shown in FIG. 2. The detection threshold for CTAB-purified genomic DNA was 250 pg with the standard PCR format (external primers), and 0.1 pg (2,500-fold lower) with the nested PCR format, based on EtBr staining and hybridization (FIG. 2). In a separate experiment, eight of eight and for of six samples containing 1.0 and 0.1 pg were positive with nested primers. The most dilute sample in that experiment contained 0.02 pg, and two of four samples were weakly positive (weak bands) by nested PCR. Assuming a genome size for *P.s. phaseolicola* equal to that of *Pseudomonas aeruginosa* (i.e., 5.85 Mb) (Holloway et al. 1990. Chromosome organization in *Pseudomonas aeruginosa* and *Pseudomonas putida*. pp. 269–278 in: *Pseudomonas: Biotransformations, Pathogenesis and Evolving Biotechnology*. Silver et al., eds. American Society for Microbiology, Washington, D.C.; Jansing and Rudolph, supra), 250 and 0.02 pg DNA corresponds to $\approx4\times10^4$ and 3 to 15 genome equivalents, respectively. Calculations were based on Avogadro's standard number, where 1.0 mol of *P.s. phaseolicola* genomes contain $6.023\times10^{23}$ molecules, and one genome equivalent is approximately 6.3 fg.

Example VII

Detection of *P.s. phaseolicola* in Bean Seed Extracts by BIO-PCR

Commercial bean seeds (cv. Great Northern White) were obtained from seed companies in California and from a grocery store in Frederick, Md. A pool of 2 kg of these seed stocks that had approximately $1\times10^4$ cfu of saprophytic bacteria/ml of seed wash was selected for quantifying the detection thresholds. The mixture was negative for *P.s. phaseolicola,* based on several agar plating (Mohan and Schaad, supra) and PCR assays (described below).

Seed-water extracts were prepared by soaking 225 g (≈1,000) seeds overnight in 500 ml of 0.02% Tween 20 in sterile water, as described by Mohan & Schaad (supra). Aliquots (0.1 ml) of the seed extracts were plated in triplicate onto KB and MSP agars to determine bacterial populations and confirm the absence of *P.s. phaseolicola.* A second set of aliquots (1 ml) were stored at −20° C. and analyzed later by direct PCR (without DNA extraction or other treatments) using the standard or nested format described above. A third set of aliquots were used to prepare seed extract stocks containing the following expected numbers of cfu of *P.s. phaseolicola* per 0.1 ml: 10–20, 1.0–2.0 and <1.0. These stocks were made by mixing 0.5 ml of serially diluted aliquots of an overnight culture (adjusted to 0.1 $OD_{600}$) with 4.5 ml of undiluted or $10^{-1}$ diluted seed extract. Similarly, 0.5 ml of each the above dilutions of the bacterial culture were mixed with 4.5 ml of SDDW (water control), to determine actual numbers of *P.s. phaseolicola* added. Each of the seed extract mixtures and water controls were plated onto KB agar plates (0.1 ml/plate). Extract treatments with expected *P.s. phaseolicola* numbers of 10–20, 1.0–2.0 and <1.0 consisted of two, eight, and eight plates, respectively. Water control treatments with the same pathogen numbers consisted of two, four, and eight plates, respectively. One-half of the plates from each mixture and control treatments were incubated for 4 days to determine the actual number of cfu of saprophytic bacteria and *P.s. phaseolicola.* The remaining plates from each mixture or control were incubated for 45 hours (*P.s. phaseolicola* colonies≈0.5–1.0 mm in diameter), washed individually three times, each time with 1 ml of SDDW. The combined washes from each plate (total volume 3 ml) were used directly for PCR analysis (35 cl/reaction), as described above or stored at −20° C. This experiment was repeated twice.

In preliminary experiments, diluted aliquots of pure culture of *P.s. phaseolicola* containing $10^3$ cfu/ml were normally positive when tested by direct nested PCR whereas seed extracts containing the same number of cells added after soaking were often negative. In contrast, similar extracts with as few as 10 added cfu of *P.s. phaseolicola*/ml were positive when tested by BIO-PCR . In a representative BIO-PCR experiment, six of eight PCR samples from washings of separate agar plates containing approximately 110 saprophytic colonies each and 1 or 2 colonies of *P.s. phaseolicola* (based on the water control plates), were positive by nested PCR (Table I). No *P.s. phaseolicola* was observed on KB or MSP agar plates of assays of aliquots of the seed extracts removed prior to adding *P.s. phaseolicola.* Both control samples (1 ml) of seed extract stored at −20° C. and assayed later by direct nested PCR were negative.

Example VIII

Detection of Tox$^-$ Strains

None of the six tox$^-$ strains caused formation of chlorotic halos, although they all produced water-soaked lesions on the bean cultivar "Red Kidney" (K. Rudolph, personal communication). These strains were examined for the presence of tox sequences by nested PCR and by Southern hybridization analysis of both their genomic DNA (digested with EcoRI) and their amplification products by using as probe the 2.6-kb EcoRI fragment originating from the tox gene cluster of strain NPS3121 (Prosen et al., supra). Pseudonomas strains and *E. coli* were grown at 18°–20° C. and 37° C., respectively, for the phaseolotoxin assay. Production of phaseolotoxin was determined by the standard microbiological assay (Staskawicz and Panopoulos. 1979. *Phytopathology*. vol. 69, pp. 663–666) using *E. coli* HB101 as the indicator and strains NPS3121 and 4419 of *P.s. phaseolicola* as positive controls.

The use of the tox gene cluster, either as a DNA probe (Schaad et al., supra) or as a PCR target (Prosen et al., supra), or the phaseolotoxin assay itself (Jansing and Rudolph, supra) to detect *P.s. phaseolicola* in bean seed has the possible disadvantage that "haloless" (toxin non-producing) strains (Johnson, J. C. 1969. *Queensl. J. Agric. Anim. Sci.* vol. 26, pp. 293–302; Mitchell, R. E. 1978. *Physiol. Plant Pathol.* vol. 13, pp. 37–49) could go undetected. Although tox⁻ strains in general apparently have little or no epidemiological importance in halo blight of beans, they are still pathogenic (Johnson, supra; Mitchell, supra; Peet et al., supra). Naturally-occurring tox⁻ strains have not been genetically characterized. It is possible that such strains contain silent tox clusters or portions thereof, and thus, can potentially revert to tox⁺ phenotype in nature. Accordingly, six tox⁻ strains (GSPB592, GSPB593, GSPB606, GSPB607, GSPB612 and GSPB792) were examined. The latter four strains gave the expected 0.5 and 0.45 bands after standard nested PCR, respectively, and their total DNA extracts contained the 2.6 EcoRI tox gene fragment, based on Southern hybridization (Table 2). Strains GSPB592 and GSPB593 did not give any PCR bands and did not contain any homology to the above probe. Strain GSPB792, although assumed to be tox⁻ (based on its inability to form chlorotic halos on bean), produced phaseolotoxin, as determined by the *E. coli* microbiological assay the other five GSPB strains did not produce an detectable toxin.

All of the references cited hereinabove are herein incorporated by reference.

TABLE 1

Detection of *Pseudomonas syringae* pv. *phaseolicola* (PSP) added to bean seed extracts by BIO-PCR.

| Seed extract dilution or water control | Expected PSP cfu/ Plate | Plate Group | Observed no. cfu/plate | | Presence of 0.45 kb band |
|---|---|---|---|---|---|
| | | | PSP | Other Bacteria | |
| Undiluted | 10–20 | I | 0² | Cʰ | NA |
| | | II | NA | NA | + |
| Water control | 10–20 | I | 12 | 0 | NA |
| | | II | NA | 0 | + |
| 10⁻¹ | 1–2 | I | 2; 2 | 97; 108 | NA; NA |
| | | I | 2; 2 | 122; 118 | NA; NA |
| | | II | NA; NA | NA; NA | +; − |
| | | II | NA; NA | NA; NA | +; + |
| Water control | 1–2 | I | 2; 0 | 0; 0 | NA; NA |
| | | II | NA; NA | NA; NA | +; − |
| 10⁻¹ | <1 | I | 0; 0 | 106; 105 | NA; NA |
| | | I | 0; 0 | 85; 115 | NA; NA |
| | | II | NA; NA | NA; NA | +; + |
| | | II | NA; NA | NA; NA | −; + |

TABLE 1-continued

Detection of *Pseudomonas syringae* pv. *phaseolicola* (PSP) added to bean seed extracts by BIO-PCR.

| Seed extract dilution or water control | Expected PSP cfu/ Plate | Plate Group | Observed no. cfu/plate | | Presence of 0.45 kb band |
|---|---|---|---|---|---|
| | | | PSP | Other Bacteria | |
| Water control | <1 | I | 1; 1 | NA; NA | NA; NA |
| | | I | 0; 0 | NA; NA | NA; NA |
| | | II | NA; NA | NA; NA | +; + |
| | | II | NA; NA | NA; NA | −; − |

TABLE 2

Analysis of Tox- strains of *Pseudomonas syringae* pv *phaselicola* by nested PCR and Southern hybridization.

| Strain | Toxin Assay[a] | 0.45 kb PCR Band[b] | Southern hybridization | |
|---|---|---|---|---|
| | | | PCR-Products[c] | Genomic DNA[d] |
| NPS 3121 | + | + | + | + |
| GSPB792 | + | + | + | + |
| GSBP606 | − | + | + | + |
| GSPB607 | − | + | + | + |
| GSPB612 | − | + | + | + |
| GSBP592 | − | − | − | − |
| GSPB593 | − | − | − | − |

[a]+/−: presence/absence of inhibition zone in phaseolotoxin bioassay.
[b]+/−: presence/absence of EtBr-stained band after nested PCR.
[c,d]+/−: presence/absence of hybridizing band.

We claim:

1. A method for the detection of target DNA-containing cells or microorganisms in a sample, said method comprising a) culturing said cells or microorganisms in order to increase the number of cells or microorganisms in the sample, b) removing the cultured cells or microorganisms from culture, c) performing enzymatic amplification of a target DNA sequence of the cultured cells or microorganisms to produce amplification products by direct polymerase chain reaction, wherein said direct polymerase chain reaction is performed on said cultured cells or microorganisms without prior processing of said cultured cell or microorganism sample, and d) detecting the amplification products as an indication of the presence of target DNA-containing cells or microorganisms.

2. The method of claim 1, wherein the cells are plant or animal cells.

3. The method of claim 1, wherein the microorganisms are bacteria, fungi, viruses, plasmids or mycobacteria.

4. The method of claim 1, wherein the amplification products are detected by ethidium bromide staining or dot blot hybridization.

* * * * *